(12) United States Patent
Burt et al.

(10) Patent No.: US 11,751,759 B2
(45) Date of Patent: Sep. 12, 2023

(54) TROCARS

(71) Applicants: Baylor College of Medicine, Houston, TX (US); Texas Heart Institute, Houston, TX (US)

(72) Inventors: Bryan M. Burt, Houston, TX (US); Mahmood Khan, The Woodlands, TX (US); William Cohn, Houston, TX (US)

(73) Assignees: Baylor College of Medicine, Houston, TX (US); Texas Heart Institute, Houston, TX (US)

( * ) Notice: Subject to any disclaimer, the term of this patent is extended or adjusted under 35 U.S.C. 154(b) by 1005 days.

(21) Appl. No.: 16/094,754

(22) PCT Filed: Apr. 13, 2017

(86) PCT No.: PCT/US2017/027320
§ 371 (c)(1),
(2) Date: Oct. 18, 2018

(87) PCT Pub. No.: WO2017/184415
PCT Pub. Date: Oct. 26, 2017

(65) Prior Publication Data
US 2019/0125176 A1  May 2, 2019

Related U.S. Application Data

(60) Provisional application No. 62/325,742, filed on Apr. 21, 2016.

(51) Int. Cl.
*A61B 1/12*  (2006.01)
*A61B 17/34*  (2006.01)
(Continued)

(52) U.S. Cl.
CPC .......... *A61B 1/126* (2013.01); *A61B 1/00006* (2013.01); *A61B 1/015* (2013.01);
(Continued)

(58) Field of Classification Search
CPC ... A61B 1/126-127; A61B 1/12; A61B 90/70; A61B 2090/701; A61B 1/015;
(Continued)

(56) References Cited

U.S. PATENT DOCUMENTS 2,264,746 A  12/1941 Ellwood
4,635,949 A  1/1987 Lucas et al.
(Continued)

FOREIGN PATENT DOCUMENTS

CA  2842217 A1  3/2008
CN  1905832 A   1/2007
(Continued)

OTHER PUBLICATIONS

Communication—Extended European Search Report, European Patent Application No. 17786362.8, dated Jan. 13, 2020, 5 pages.
(Continued)

*Primary Examiner* — Ryan N Henderson
*Assistant Examiner* — Pamela F Wu

(57) ABSTRACT

One aspect of the invention provides a trocar including: a central cylinder defining a central channel and having a distal end adapted and configured for insertion within a subject; one or more gas outlets located within the central cylinder proximate to the distal end of the trocar; and one or more liquid outlets located within the central cylinder on a proximal side of the one or more gas outlets. The one or more liquid outlets are adapted and configured to dispense a liquid when an endoscope is withdrawn from a fully extended position within the central channel of the trocar to a position proximate to the one or more liquid outlets. Distal (Continued)

advancement of the endoscope to a position adjacent to the one or more gas outlets removes liquid from a distal end of the endoscope.

18 Claims, 15 Drawing Sheets

(51) Int. Cl.

| | |
|---|---|
| G02B 23/24 | (2006.01) |
| A61B 90/70 | (2016.01) |
| A61B 1/00 | (2006.01) |
| A61B 1/015 | (2006.01) |
| A61M 13/00 | (2006.01) |

(52) U.S. Cl.
CPC .......... *A61B 17/34* (2013.01); *A61B 17/3421* (2013.01); *A61B 17/3478* (2013.01); *A61B 90/70* (2016.02); *A61M 13/003* (2013.01); *G02B 23/2476* (2013.01); *A61B 17/3417* (2013.01); *A61B 2217/007* (2013.01)

(58) Field of Classification Search
CPC . A61B 1/012; A61B 17/3421; A61B 17/3478; A61B 1/00082; A61B 1/00154; A61B 1/00156; A61B 1/267; A61B 1/313–32; A61B 17/34; A61B 17/3437; A61B 17/3474; A61B 90/701–702; A61B 17/3417; A61B 17/3419; A61B 2217/00; A61B 2217/007; A61M 3/00; A61M 17/3423; A61M 2017/3427; A61M 2017/3445; A61M 17/3498; G02B 23/00; G02B 23/24; G02B 23/2476; G02B 23/2484
USPC ........... 600/114, 115–116; 606/101.01–101.4
See application file for complete search history.

(56) References Cited

U.S. PATENT DOCUMENTS

| | | | |
|---|---|---|---|
| 4,800,869 A | | 1/1989 | Nakajima |
| 4,852,551 A | | 8/1989 | Opie et al. |
| 5,274,874 A | | 1/1994 | Cercone et al. |
| 5,386,817 A | * | 2/1995 | Jones ................. A61B 1/00135 600/125 |
| 5,429,596 A | | 7/1995 | Arias et al. |
| 5,476,447 A | | 12/1995 | Noda et al. |
| 5,573,494 A | | 11/1996 | Yabe et al. |
| 5,575,756 A | | 11/1996 | Karasawa et al. |
| 5,697,888 A | * | 12/1997 | Kobayashi ......... A61B 1/00068 600/157 |
| 6,126,592 A | | 10/2000 | Proch et al. |
| 6,126,593 A | | 10/2000 | Honda et al. |
| 7,771,384 B2 | | 8/2010 | Ravo |
| 8,057,443 B2 | | 11/2011 | McNeil |
| 8,672,890 B2 | | 3/2014 | Franer et al. |
| 8,690,764 B2 | | 4/2014 | Clark et al. |
| 8,690,831 B2 | | 4/2014 | Duke |
| 8,915,842 B2 | | 12/2014 | Weisenburgh, II et al. |
| 9,211,059 B2 | | 12/2015 | Drach et al. |
| 11,583,176 B2 | | 2/2023 | Aluru et al. |
| 2005/0077689 A1 | | 4/2005 | Hueil |
| 2006/0161045 A1 | | 7/2006 | Merril et al. |
| 2006/0293559 A1 | | 12/2006 | Grice, III et al. |
| 2007/0282253 A1 | * | 12/2007 | Sasaki ................... A61B 1/313 604/93.01 |
| 2008/0255424 A1 | | 10/2008 | Durgin et al. |
| 2009/0253966 A1 | | 10/2009 | Ichimura |
| 2009/0270818 A1 | * | 10/2009 | Duke ................. A61B 17/3462 604/272 |
| 2009/0312783 A1 | | 12/2009 | Whayne et al. |
| 2011/0152776 A1 | * | 6/2011 | Hartoumbekis ....... A61B 1/126 604/164.01 |
| 2012/0022331 A1 | | 1/2012 | Poll et al. |
| 2013/0053643 A1 | * | 2/2013 | Yoshida ................. A61B 1/126 600/114 |
| 2014/0188038 A1 | * | 7/2014 | Stearns .............. A61B 17/3421 604/24 |
| 2014/0371763 A1 | | 12/2014 | Poll et al. |
| 2015/0190041 A1 | * | 7/2015 | Suehara ................. A61B 1/128 600/109 |
| 2017/0078583 A1 | | 3/2017 | Haggerty et al. |
| 2018/0078120 A1 | | 3/2018 | Poll et al. |
| 2020/0163541 A1 | | 5/2020 | Holsten |
| 2020/0375444 A1 | | 12/2020 | Coffeen et al. |
| 2021/0127963 A1 | | 5/2021 | Aluru et al. |
| 2021/0127964 A1 | | 5/2021 | Aluru et al. |
| 2022/0192480 A1 | | 6/2022 | Burt et al. |

FOREIGN PATENT DOCUMENTS

| | | |
|---|---|---|
| CN | 101170941 A | 4/2008 |
| CN | 101296648 A | 10/2008 |
| CN | 101627894 A | 1/2010 |
| CN | 101668474 A | 3/2010 |
| CN | 202446249 U | 9/2012 |
| CN | 103957769 A | 7/2014 |
| CN | 104379045 A | 2/2015 |
| CN | 104720733 A | 6/2015 |
| CN | 204636289 U | 9/2015 |
| CN | 105310636 A | 2/2016 |
| EP | 2111808 A2 | 10/2009 |
| EP | 2886037 A1 | 6/2015 |
| JP | 7-289501 A | 11/1995 |
| JP | 2009261948 A | 11/2009 |
| JP | 2013048821 A | 3/2013 |
| WO | 02100455 A2 | 12/2002 |
| WO | WO2006039646 A2 | 4/2006 |
| WO | WO-2010046891 A2 | 4/2010 |
| WO | 2012066992 A1 | 5/2012 |
| WO | WO2013012790 A2 | 1/2013 |
| WO | WO-2013183014 A1 | 12/2013 |
| WO | 2014050571 A1 | 4/2014 |
| WO | WO-2017184415 A1 | 10/2017 |
| WO | WO-2022235262 A1 | 11/2022 |

OTHER PUBLICATIONS

Notice of Reasons for Rejection, Japanese Patent Application No. 2018-555658, dated Jan. 20, 2021.
Mckenna, Daniel et al., "A Novel Device Maintaining Clear Optics During Surgery", floshield.com/images/literature/Floshield-Lit_SAGES.pdf, downloaded May 23, 2019.
First Office Action, China Patent Application No. 2017800379560, dated Dec. 1, 2020.
International Search Report and Written Opinion, International Patent Application No. PCT/US2017/027320, Jul. 17, 2017.
Amazon.com: Morris Products 70332 Roller Ball Contacts, Open, Circuit . . . , http://www.amazon.com/Morris-Products-70332-Contacts-Circuit/dp/B . . . , downloaded Mar. 16, 2016.
Insinkerator, Food Waste Disposer, Sink Top Switch, downloaded Mar. 16, 2016.
MedGadget, Endopath Xcel Trocar with Optiview Keeps the Lens Clean for Superior Visualization, http://www.medgadget.com/2010/03/endopath_xcel_trocar_with-optivie . . . , downloaded Mar. 16, 2016.
Wikipedia, "Trocar", https://en.wikipedia.org/wiki/Trocar, downloaded Mar. 16, 2016.
Non-Final Office Action for U.S. Appl. No. 16/690,979 dated Jul. 15, 2022, 20 pages.
Office Action for Chinese Application No. 20178037956, dated Jun. 10, 2022, 16 pages.
International Search Report and Written Opinion for International Application No. PCT/US2021/030700 dated Jan. 25, 2022, 16 pages.

(56) References Cited

OTHER PUBLICATIONS

Office Action for Australian Application No. 2017253708, dated Mar. 18, 2022, 4 pages.
Non-Final Rejection for U.S. Appl. No. 17/692,550, dated Aug. 31, 2022, 21 pages.
Huang et al. "A comprehensive study of low-power operation in IEEE 802.15. 4. In Proceedings of the 10th ACM Symposium on Modeling, analysis, and simulation of wireless and mobile systems" Oct. 23, 2007, pp. 405-408.
Office Action for Japanese Application No. JP2021184037, dated Nov. 14, 2022, 6 pages.
Office Action for Chinese Application No. 201780037956.0, dated Nov. 24, 2022, 12 pages.
Office Action Issued in U.S. Appl. No. 16/690,996, dated Jan. 24, 2023.
Office Action for Australian Application No. AU2022202336A1 dated May 12, 2023, 04 pages.

\* cited by examiner

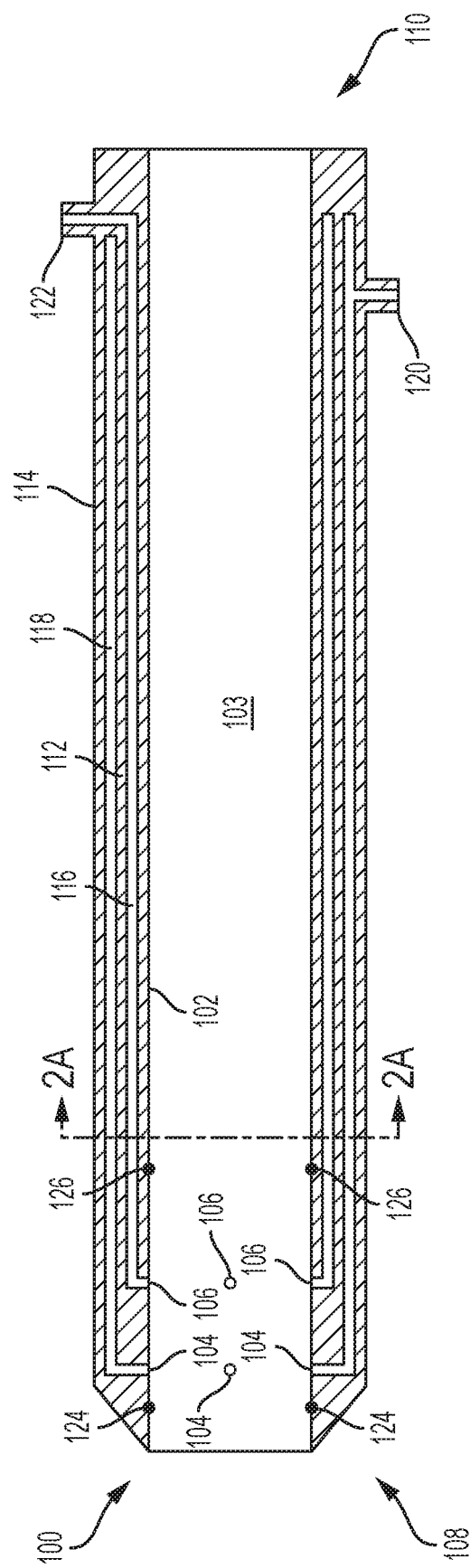
FIG. 1
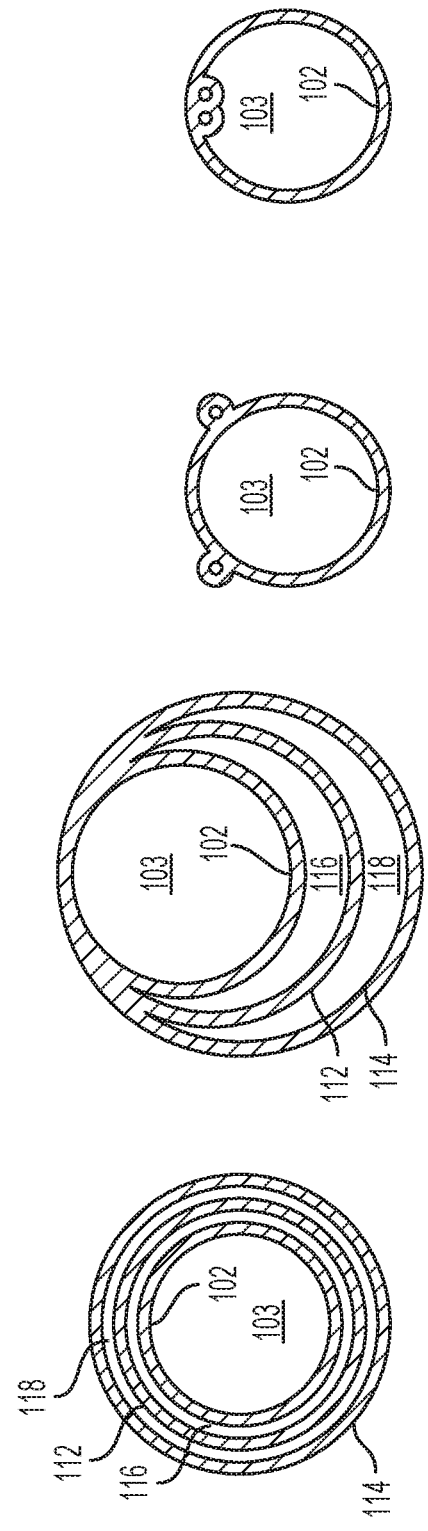

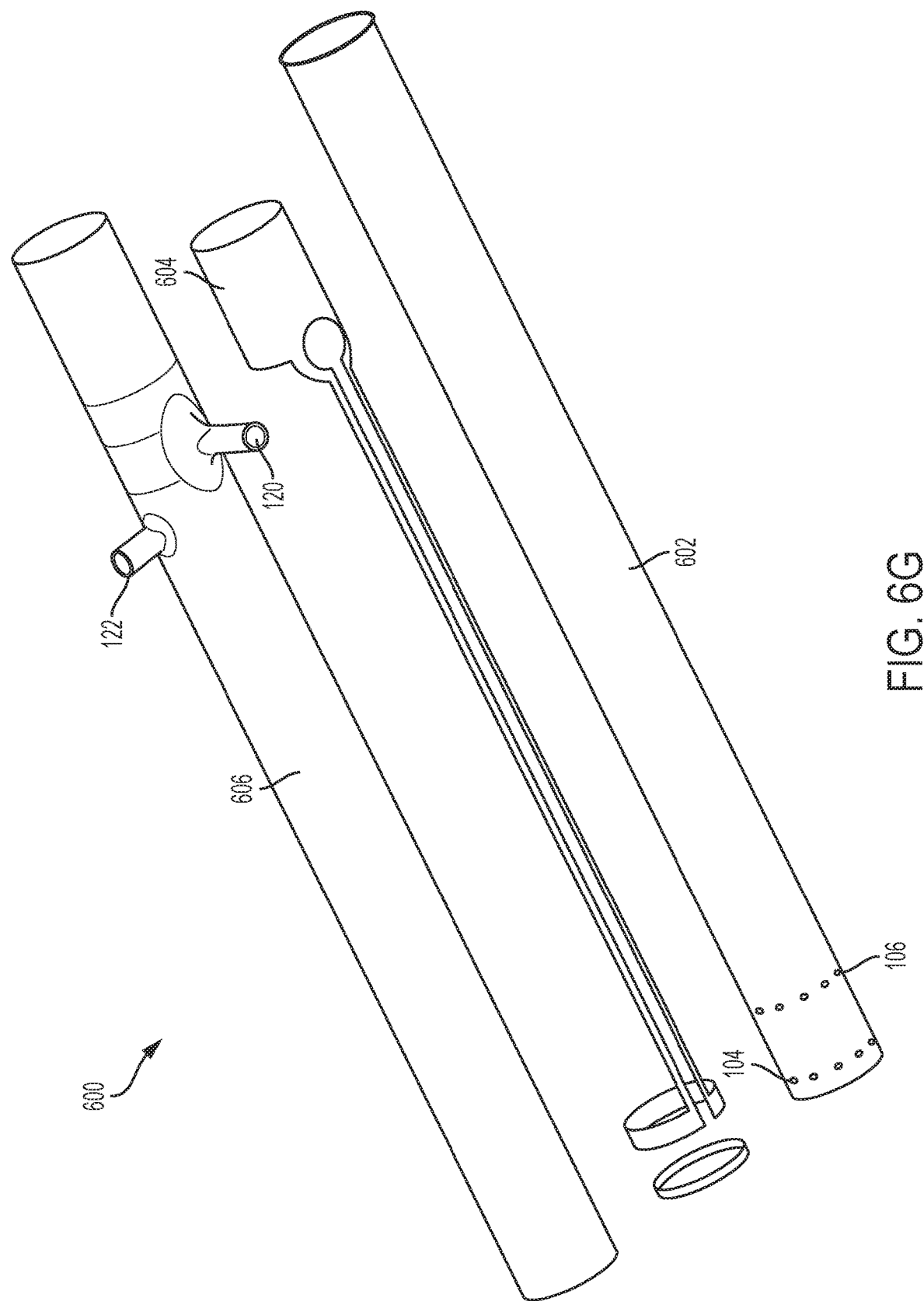

TROCARS

CROSS-REFERENCE TO RELATED APPLICATION

This application is a national phase application under 35 U.S.C. 371 of International Application No. PCT/US2017/027320, filed Apr. 13, 2017, which claims priority to U.S. Provisional Patent Application Ser. No. 62/325,742 filed Apr. 21, 2016. The entire contents of each application is hereby incorporated by reference herein.

BACKGROUND OF THE INVENTION

Surgical endoscopic camera devices, or endoscopes, are utilized in minimally invasive surgery to visualize the operative field. The endoscope is inserted into a body cavity through a trocar that is employed as a portal for surgical instruments. Carbon dioxide insufflation is often delivered through these trocars into the body cavity to facilitate expansion of the body cavity, thereby providing working room for the operation. Endoscopes typically contain a means of illumination such as a fiber optic light source and a means of imaging such as video camera.

During minimally invasive surgical procedures utilizing endoscopes, the lens of the endoscope will often encounter blood, cautery smoke, or debris, decreasing visualization of the operative field. Typically, in order to remove the visual obstruction the lens of the endoscope must be cleaned. Cleaning of the endoscope typically requires the operator to remove the scope from the patient and manually clean the endoscopic camera lens. This exercise, which is often performed countless times during a minimally invasive surgical procedure, results in repeated loss of visualization of the operative field, significantly increased operative time, increased surgeon frustration, and increased possibility of untoward surgical outcomes.

SUMMARY OF THE INVENTION

One aspect of the invention provides a trocar including: a central cylinder defining a central channel and having a distal end adapted and configured for insertion within a subject; one or more gas outlets located within the central cylinder proximate to the distal end of the trocar; and one or more liquid outlets located within the central cylinder on a proximal side of the one or more gas outlets. The one or more liquid outlets are adapted and configured to dispense a liquid when an endoscope is withdrawn from a fully extended position within the central channel of the trocar to a position proximate to the one or more liquid outlets. Distal advancement of the endoscope to a position adjacent to the one or more gas outlets removes liquid from a distal end of the endoscope.

This aspect of the invention can have a variety of embodiments. The one or more liquid outlets can be positioned between about 1 cm and about 5 cm proximal of the one or more gas outlets. The one or more liquid outlets can be positioned within about 6 cm of the distal end of the trocar.

The trocar can further include a first coaxial cylinder surrounding at least a portion of the central cylinder. The first coaxial cylinder can define a substantially cylindrical channel extending to the one or more liquid outlets.

The trocar can further include a gasket positioned between the central cylinder and the first coaxial cylinder. The gasket can define a confined liquid passage to the one or more liquid outlets. The gasket can further define a confined gas passage to the one or more gas outlets. The trocar can further include a liquid inlet in fluid communication with the first coaxial cylinder.

The trocar can further include a second coaxial cylinder surrounding at least a portion of the first coaxial cylinder. The second coaxial cylinder can define a substantially cylindrical channel extending to the one or more gas outlets.

The trocar can further include a valve adapted and configured to control flow of the liquid to the one or more liquid outlets. The valve can be an electromechanically actuated valve. The valve can be a pneumatically actuated valve.

The trocar can further include a sensor adapted and configured to detect when a distal end of the endoscope is proximate to the one or liquid outlets. The sensor can be adapted and configured to communicate directly or indirectly to control flow of the liquid to the one or more liquid outlets. The sensor can be selected from the group consisting of: a mechanical sensor, a magnetic sensor, a magnetic reed switch, an optical sensor, and a Hall sensor. The sensor can be located proximate to the distal end of the central cylinder. The sensor can be located proximate to the one or more liquid outlets. The sensor can be located proximate to the proximal end of the central cylinder.

The trocar can further include a controller in communication with the sensor. The controller can be adapted and configured to control flow to the liquid outlets so that a liquid is expelled from the liquid ports when the distal end of the endoscope is proximate to the liquid outlets.

The trocar can further include an override switch. The override switch can be coupled to an endoscope. The controller can be in communication with the override switch and further adapted and configured to control flow to the liquid outlets so that a liquid is expelled from the liquid ports when the override switch is actuated.

The trocar can further include a manual switch adapted and configured to communicate directly or indirectly to control flow of the liquid to the one or more liquid outlets. The manual switch can be disposed on a handle of said endoscope. The manual sensor can include a foot pedal.

Another aspect of the invention provides a trocar including: a central cylinder defining a central channel and having a distal end adapted and configured for insertion within a subject; one or more gas outlets located within the central cylinder proximate to the distal end of the trocar; one or more liquid outlets located within the central cylinder on a proximal side of the one or more gas outlets, wherein the one or more liquid outlets are adapted and configured to dispense a liquid when an endoscope is withdrawn from a fully extended position within the central channel of the trocar to a position proximate to the one or more liquid outlets; an outer cylinder surrounding at least a portion of the central cylinder; a gas inlet located at a proximal end of the outer cylinder; a liquid inlet located at the proximal end of the outer cylinder; a gasket positioned between the central cylinder and the outer cylinder, the gasket defining: a confined gas passage between gas inlet and the one or more gas outlets; and a confined liquid passage between liquid inlet and the one or more liquid outlets; and one or more sensors adapted and configured to detect when a distal end of the endoscope is proximate to the one or liquid outlets. The one or more sensors are adapted and configured to communicate directly or indirectly with a valve to control flow of the liquid to the one or more liquid outlets.

This aspect of the invention can have a variety of embodiments. The confined liquid passage can have a cross-sectional area at least 10 times a combined cross-section area of the one or more liquid outlets. The confined gas passage can have a cross-sectional area at least 10 times a combined cross-section area of the one or more gas outlets.

BRIEF DESCRIPTION OF THE DRAWINGS

For a fuller understanding of the nature and desired objects of the present invention, reference is made to the following detailed description taken in conjunction with the accompanying drawing figures wherein like reference characters denote corresponding parts throughout the several views.

FIG. 1 is an longitudinal cross-section of a trocar according to an embodiment of the invention.

FIGS. 2A-2D depict exemplary axial cross-sections of a trocar according to embodiments of the invention.

FIGS. 6A-6H depicts a two-lumen trocar according to an embodiment of the invention.

DEFINITIONS

Figure 3A:
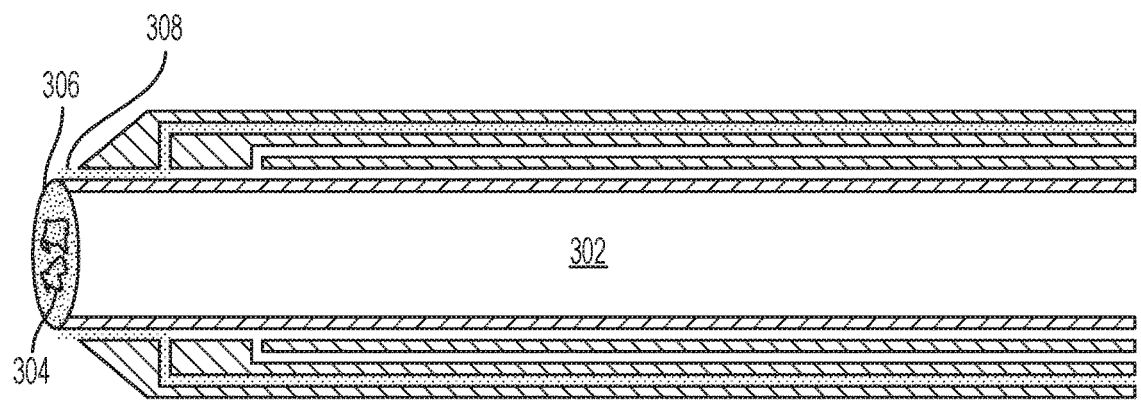
FIGS. 3A-3D provides a series of longitudinal cross-sections depicting an exemplary mode of operation of a trocar according to an embodiment of the invention.

The instant invention is most clearly understood with reference to the following definitions.

As used herein, the singular form "a," "an," and "the" include plural references unless the context clearly dictates otherwise.

Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

As used in the specification and claims, the terms "comprises," "comprising," "containing," "having," and the like can have the meaning ascribed to them in U.S. patent law and can mean "includes," "including," and the like.

Unless specifically stated or obvious from context, the term "or," as used herein, is understood to be inclusive.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 (as well as fractions thereof unless the context clearly dictates otherwise).

DETAILED DESCRIPTION OF THE INVENTION

One embodiment of the invention provides an access trocar that automatically cleans the endoscopic camera used in minimally invasive surgery including but not limited to laparoscopy and thoracoscopy. Further embodiments of the invention provide a system for and method of cleaning a surgical endoscopic camera lens to optimize the viewing experience during operation.

Embodiments of the invention provide an access device for minimally invasive surgery through which an endoscopic camera can be introduced into a body cavity and which has a mechanism for automatic cleaning of the camera within the device. The device can be a trocar that contains two separate channel systems for separate delivery of: (1) saline for cleaning of the lens of the camera and (2) carbon dioxide ($CO_2$) that is routinely used for insufflation of body cavities in minimally invasive surgery, and which here can also be used to clear the lens of the residual saline with which it has been rinsed. Each of the channels can run along the length of the trocar and have an exit site (for either the saline or the $CO_2$) located at the distal end of the trocar, which is the end located within the body cavity. Each of these channels can be connected separately to both an ex vivo source of saline and of $CO_2$, which can be delivered through tubing attached to the lumens of the trocar device.

A variety of mechanisms are described for activation of the saline rinse. One mechanism utilizes a sensor that is located within the trocar that can sense when the endoscopic camera is withdrawn into the trocar and which will signal delivery of pressurized saline to the lens of the camera. Another mechanism is a surgeon-activated mechanism by which the surgeon can engage a button that activates delivery of the saline rinse to the lens of the camera when the endoscopic camera is drawn into the trocar. The button mechanism can be a button that is situated with the saline tubing, between the ex vivo reservoir of saline and the trocar, and which can be attached to the camera itself so that it is easily pressed by the camera operator's finger. Following delivery of saline by either of these two mechanisms, as the endoscopic camera is reinserted into the body cavity, it can meet the constant stream of carbon dioxide at the most distal end of the trocar, which rids the camera lens of any residual saline.

Exemplary Trocars

Referring now to FIG. 1, one embodiment of the invention provides a trocar 100 including a central cylinder 102 defining a central channel 103, one or more (e.g., 1, 2, 3, 4, and the like) gas outlets 104, and one or more (e.g., 1, 2, 3, 4, and the like) liquid outlets 106. The gas outlets 104 and liquid outlets 106 can be arranged at various radial positions and in a single distal depth or at varying distal depths. For example, gas outlets 104 and liquid outlets 106 can be arranged along a ring perpendicular to a central axis of the central channel 103, for example, 2 outlets spaced about 180° apart, 3 outlets spaced about 120° apart, 4 outlets spaced about 90° apart, and the like.

Trocar 100 can have a distal end 108 adapted and configured for insertion within a subject and a proximal end 110 adapted and configured to remain outside of a subject. For example, distal end 108 can be sharpened and/or beveled to pierce a subject and to access a body cavity. Trocar 100 can be fabricated from a variety of materials such as metals (e.g., stainless steel), polymers, plastics, and the like using a variety of techniques including casting, molding, machining, thermomolding, thermosetting, injection molding, vacuum forming, additive manufacturing (also known as 3D printing), and the like.

Trocar 100 can have a variety of dimensions to accommodate various surgical needs. For example, the inner diameter of central channel 103 can be about 5 mm, about 10 mm, about 12 mm, and the like. Trocar 100 can have a variety of lengths such as about 75 mm and about 100 mm.

Gas outlets 104 can be located within the central cylinder 102 proximate the distal end 108. For example, gas outlets 104 can have a distance from the distal end 108 (e.g., measured from the furthest point parallel to the central axis of the trocar 100) between about 0 cm and about 1 cm, between about 1 cm and about 2 cm, between about 1.5 cm and about 2.5 cm, between about 2 cm and about 3 cm, and the like Liquid outlets 106 can be located within the central cylinder 102 on a proximal side of the one or more gas outlets 104. For example, liquid outlets 106 can have a distance from the gas outlets 104 (e.g., measured parallel to the central axis of the trocar 100) between about 0 cm and about 1 cm, between about 1 cm and about 2 cm, between about 2 cm and about 3 cm, between about 3 cm and about 4 cm, between about 3.5 cm and about 4.5 cm, and the like.

Gas outlet(s) 104 and/or liquid outlet(s) 106 can have a shape and/or size sufficient to generate sufficient liquid flow to reach the center of the central cylinder 102 and clean a lens of an endoscope. For example, gas outlet(s) 104 and/or liquid outlet(s) 106 can have a diameter or largest-cross-sectional dimension selected between about 0.1 mm and about 3 mm. In one embodiment, the liquid outlets 106 are angled retrograde within the trocar 100 such that the exiting liquid is directed back toward the lens of the endoscope.

Gas outlet(s) 104 and/or liquid outlet(s) 106 can have smaller cross-sectional dimensions than the channels supplying gas and liquid in order to produce increased gas and/or liquid velocity. For example, the combined cross-sectional area of the outlet(s) 104 and/or liquid outlet(s) 106 can be less than the cross-sectional area of a supplying gas or liquid channel by a factor of at least about 10, about 100, about 1000, and the like.

Operation of the one or more liquid outlets 106 can be adapted, configured, and/or programmed to dispense a liquid when an endoscope is withdrawn from a fully extended position within the central channel 102 of the trocar 100 to a position proximate to the one or more liquid outlets 106 as further described herein.

Exemplary Modes of Operation

FIGS. 3A-3D illustrate an exemplary mode of operation.

In FIG. 3A, an endoscope 302 is distally advanced within the trocar 100 and obstructed by debris 304 on lens 306. Gas 308 flows out of gas outlet(s) and past endoscope 302 for insufflation of the body cavity.

Figure 3B:
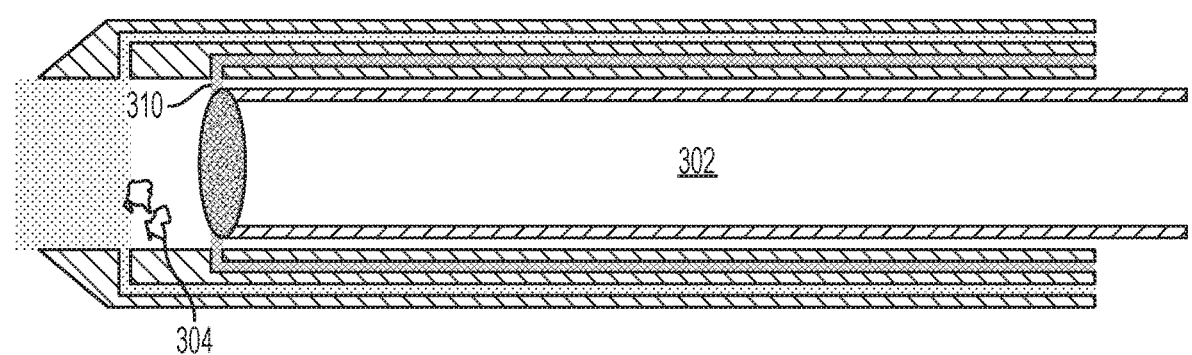

In FIG. 3B, the endoscope 302 is partially withdrawn proximally. Liquid 310 is dispensed from liquid outlet(s).

Figure 3C:
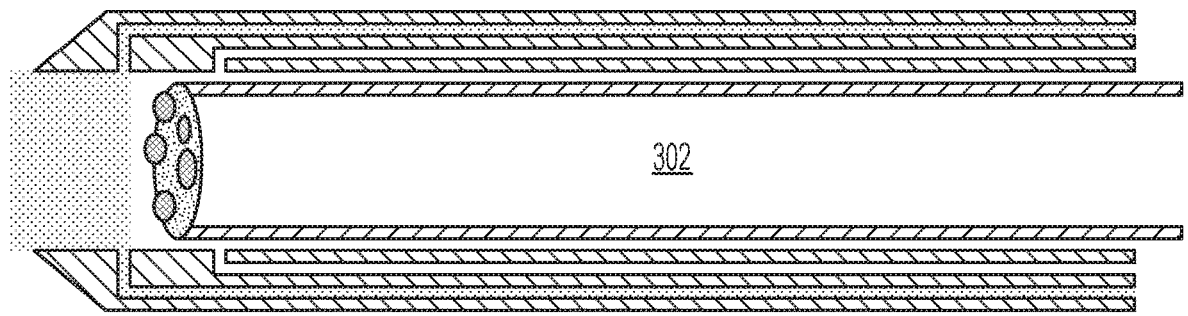

In FIG. 3C, the endoscope 302 is advanced again. Fluid flow ceases, but the lens 306 is now wet, e.g., with liquid droplets.

Figure 3D:
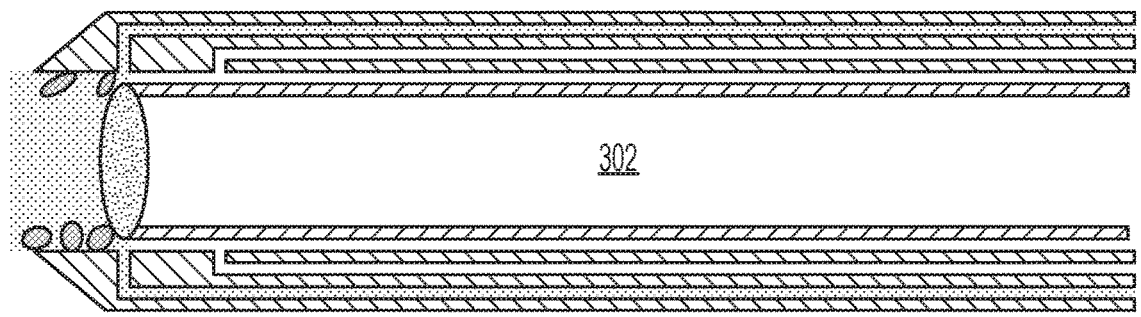

In FIG. 3D, the endoscope 302 is further advanced so that the endoscope lens 306 is adjacent to the gas outlets, which blow any liquid off of the lens 206.

Fluid Passages

Gas and liquid can be provided to gas outlets 104 and liquid outlets 106 through a variety of structures. In one embodiment, one or more conduits are arrayed inside or outside of the central channel 102 as depicted in FIGS. 2C and 2D.

Referring again to FIGS. 1 and 2A, in one embodiment, trocar 100 includes a plurality of coaxial cylinders 112, 114 surrounding central cylinder 102. Coaxial cylinders 112, 114 can define substantially cylindrical channels 116, 118 between adjacent cylinders 102, 112, 114. Expanding the cross-sectional surface area of fluid channels 116, 118 (particularly water channel 116) lowers the friction applied to the fluid within channels 116, 118. As a result, liquids and gases can be provided from gas inlet(s) 120 and liquid inlet(s) 122 to gas ports 104 and liquid ports 106, respectively, without the need for significantly elevated pressures. For example, $CO_2$ can be provided at or below the typical pressures available in operating rooms (e.g., between about 0 atmospheres and about 20 atmospheres). Likewise, liquids (e.g., saline) can be provided to the distal end 108 of the trocar 100 with minimal pressure such as those that can be generated with an hand-operated intravenous bag pressure cuff. Gas and/or liquid can be provided either to the trocar at gas inlet(s) 120 and liquid inlet(s) 122 or at gas outlet(s) 104 and/or liquid outlet(s) 106 at pressures such as between about 1 mmHg and about 15 mmHg, between about 10 mmHg and about 50 mmHg, between about 50 mmHg and about 500 mmHg, between about 500 mmHg and about 1,000 mmHg, and the like.

In another embodiment depicted in FIGS. 6A-6H, the trocar 600 includes a central cylinder 602 and an outer cylinder 606 separated by one or more gaskets 604 that define a gas passage 608 connecting gas port 120 and gas outlets 104 and a liquid passage 610 connecting liquid port 122 and liquid outlets 106. Gasket 604 can be fabricated from a variety of materials such as elastomers. In one embodiment, gasket 604 is applied (e.g., with adhesive) to either the central cylinder 602 or the outer cylinder 606. The two cylinders 602, 606 can then be assembled, e.g., through an interference fit that can be facilitated by thermal expansion of outer cylinder 606 and/or thermal contraction of central cylinder 602.

Control of Fluid Flow

In one embodiment of the invention, gas (e.g., $CO_2$) flows continuously from gas inlet 120 to gas ports 104 in order to support body cavity insufflation.

Switching of liquid flow can be provided in order to avoid flooding of the body cavity, obstruction of a downstream endoscope 302, and the like. A variety of control mechanisms can be utilized. Exemplary approaches are describe herein.

Switches, sensors, and/or other control architecture can be placed at any point along, internal to, and/or external to the trocar 100. In one embodiment, one or more switches, sensors, and/or other control architecture are located at or toward distal end 108 of trocar 100. In another embodiment, one or more switches, sensors, and/or other control architecture are located at or toward proximal end 110 of trocar 100. In still other embodiments, one or more switches, sensors, and/or other control architecture are external to the trocar 100 and, for example, mounted on or integral to an endoscope 302.

For example and referring to FIG. 1, a single switch/sensor (or array of switches/sensors) 124 can be located distal to the gas ports 104. Such an embodiment could include a control device configured to control fluid flow such that flow occurs for a defined period of time (e.g., between about 5 seconds and about 10 seconds, and the like) after the switch/sensor 124 detects withdrawal of the endoscope 302 past the switch (e.g., a change from detection of the endoscope 302 to absence of the endoscope 302). Such an event would suggest that either the surgeon is partially withdrawing the endoscope 302 for cleaning or completely withdrawing the endoscope 302 (in which case, cleaning is still desirable to avoid fouling of proximal portions of the trocar 100).

Still referring to FIG. 1, in another example, two switches/sensors (or array of switches/sensors) 124, 126 can be arranged such that a first switch/sensor 124 is located distal to liquid port(s) 106 and a second switch/sensor 126 is located proximal to liquid port(s) 106. A control device can be configured to actuate fluid flow when the second switch/sensor 126 detects the endoscope 302 and the first switch/sensor 124 does not detect the endoscope, indicating that the lens of the endoscope 302 is between the second switch/sensor 126 and the first switch/sensor 124.

In another embodiment, a sensor 126 detects the presence of a distal end of an endoscope in proximity to the liquid outlet(s) 106 and triggers liquid flow.

In still another embodiment, a sensor can be placed either on a proximal end 110 of the trocar 100 or the endoscope to detect when the endoscope is withdrawn from a distally advanced position. For example, the sensor can be placed on a flange or other axially facing surface such that full advancement of the endoscope 302 will engage the switch.

Various switches and sensors can be utilized.

In one embodiment, the switches are mechanical switches that control fluid flow based on compression and/or other physical forces. Such switches could be engaged/disengaged as the endoscope 302 is advanced or retracted through the central channel 103 of the trocar 100. For example, a ball valve (e.g., including spring-loaded ball bearings protruding into the central channel 103) or a lever protruding into central channel 103 can be depressed as the endoscope 302 is inserted.

Figure 7A:
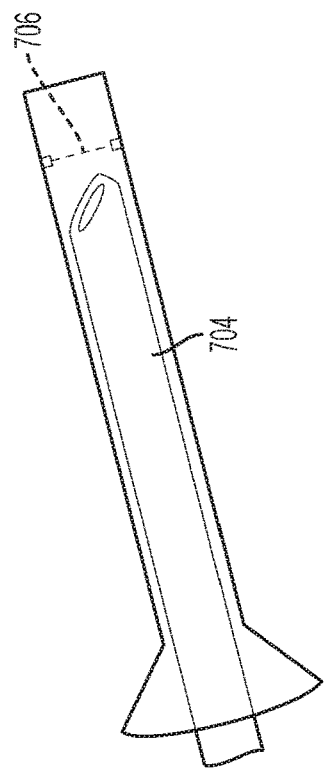
FIGS. 7A-7D depict exemplary embodiments depicting various fluid flow control devices for a trocar.

FIG. 7A illustrates an embodiment of a trocar having a mechanical switch/sensor (switch 702) for controlling fluid flow. In the illustrated embodiment, when endoscope 704 is withdrawn proximally past switch 702, the switch activates fluid flow. Further, when endoscope 704 is inserted distally past switch 702, the switch deactivates fluid flow. Switch 702 can include a lever that protrudes into a central channel such that it can be contacted and deactivated by endoscope 704. Switch 702 can be located near distal end 108 as is illustrated in FIG. 7A, or switch 702 can be located near proximal end 110. In various embodiments, more than one mechanical switch/sensor can be included. Additionally, in other embodiments, other types of mechanical switches can be implemented. For example, a ball valve can be used instead of a lever switch.

In another embodiment, the switch(es)/sensor(s) are optical switch(es)/sensor(s). For example, the switch can include an optical (e.g., laser) sensor.

Other exemplary switches/sensors include magnetic switches/sensors that can be engaged or disengaged based on ferromagnetic forces between magnets in the switches/sensors and/or the endoscope 302. One example of a magnetic switch is a magnetic reed switch such as described in U.S. Pat. No. 2,264,746.

Other exemplary sensors include a Hall effect sensor that detects a voltage difference across an electrical circuit as a magnet in an endoscope 302 is moved with respect to a sensor mounted in the trocar 100.

Figure 7B:
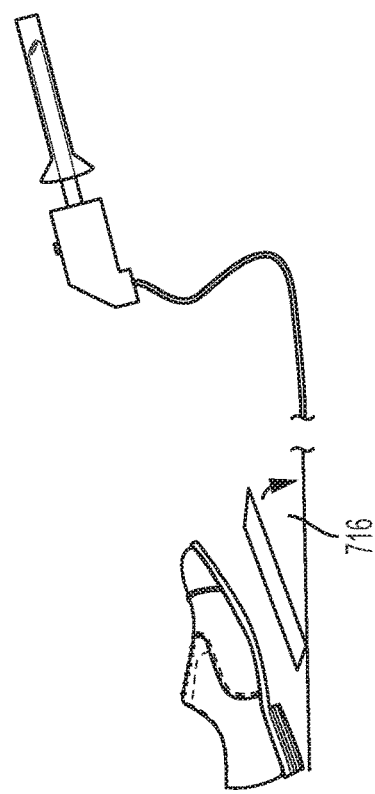

FIG. 7B illustrates an embodiment having electronic switch/sensor 706. In the illustrated embodiment, when endoscope 704 is withdrawn proximally past switch 706, the switch 706 activates fluid flow. Further, when endoscope 704 is inserted distally past switch 706, the switch 706 deactivates fluid flow. Electronic switch 706 can be any one of a magnetic switch/sensor or optical switch/sensor such that it is able to control fluid flow based on the positioning of endoscope 704. In various embodiments, more than one electronic switch/sensor can be included.

Manual Dispensing of Liquid

Figure 4:
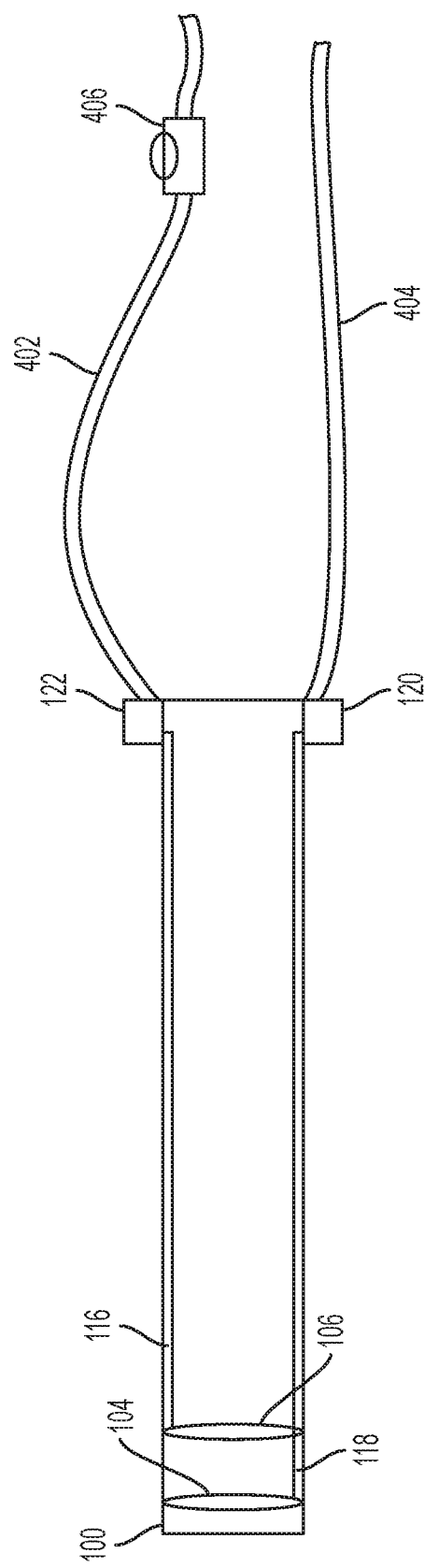
FIG. 4 depicts an assembly of a trocar and tubing for gas and liquid as well as a manual switch for saline delivery according to an embodiment of the invention.
Figure 5A:
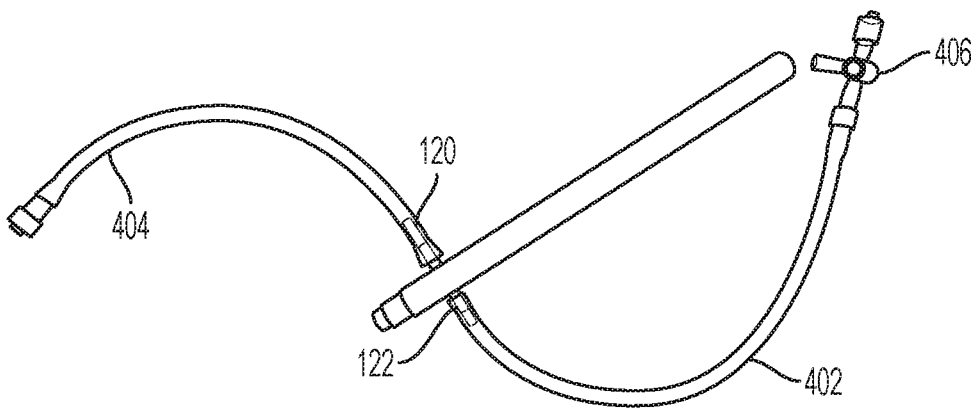
FIGS. 5A-5D depict a prototype of a trocar fabricated from copper tubing according to an embodiment of the invention.
Figure 5B:
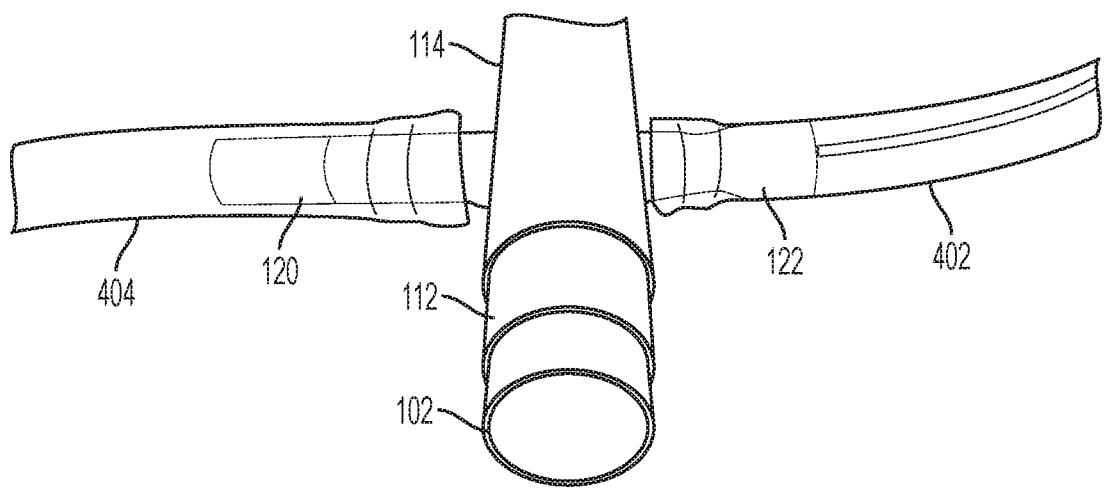
Figure 5C:
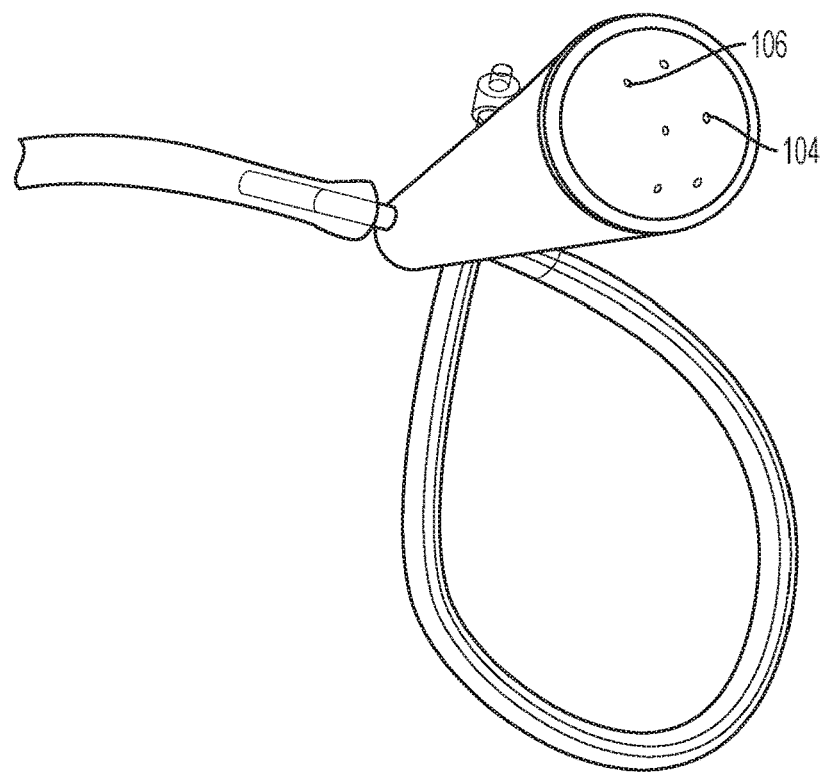
Figure 5D:
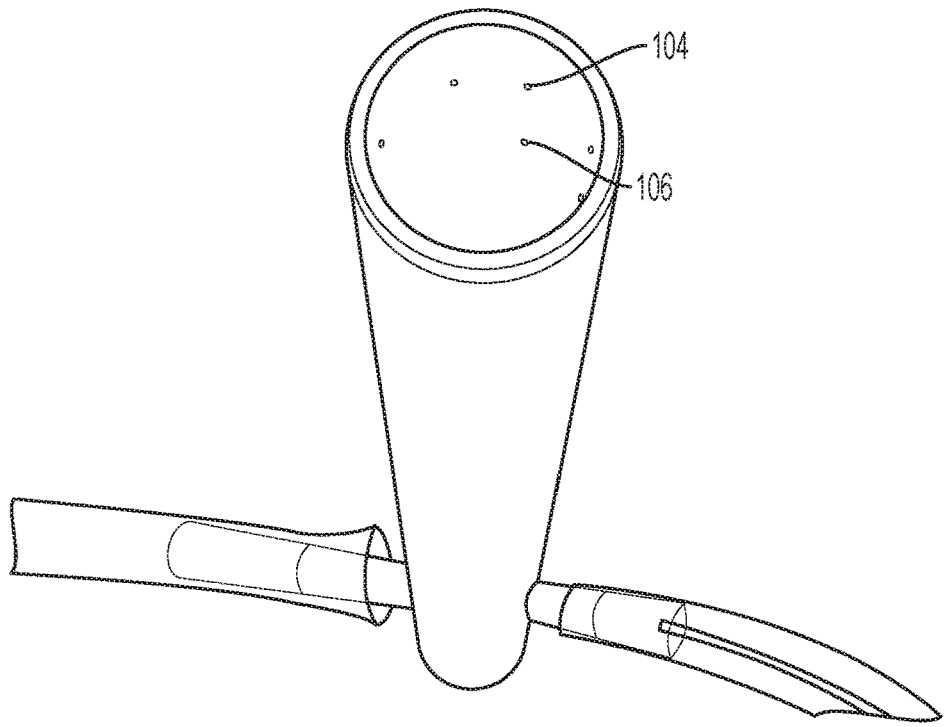
Figure 6A:
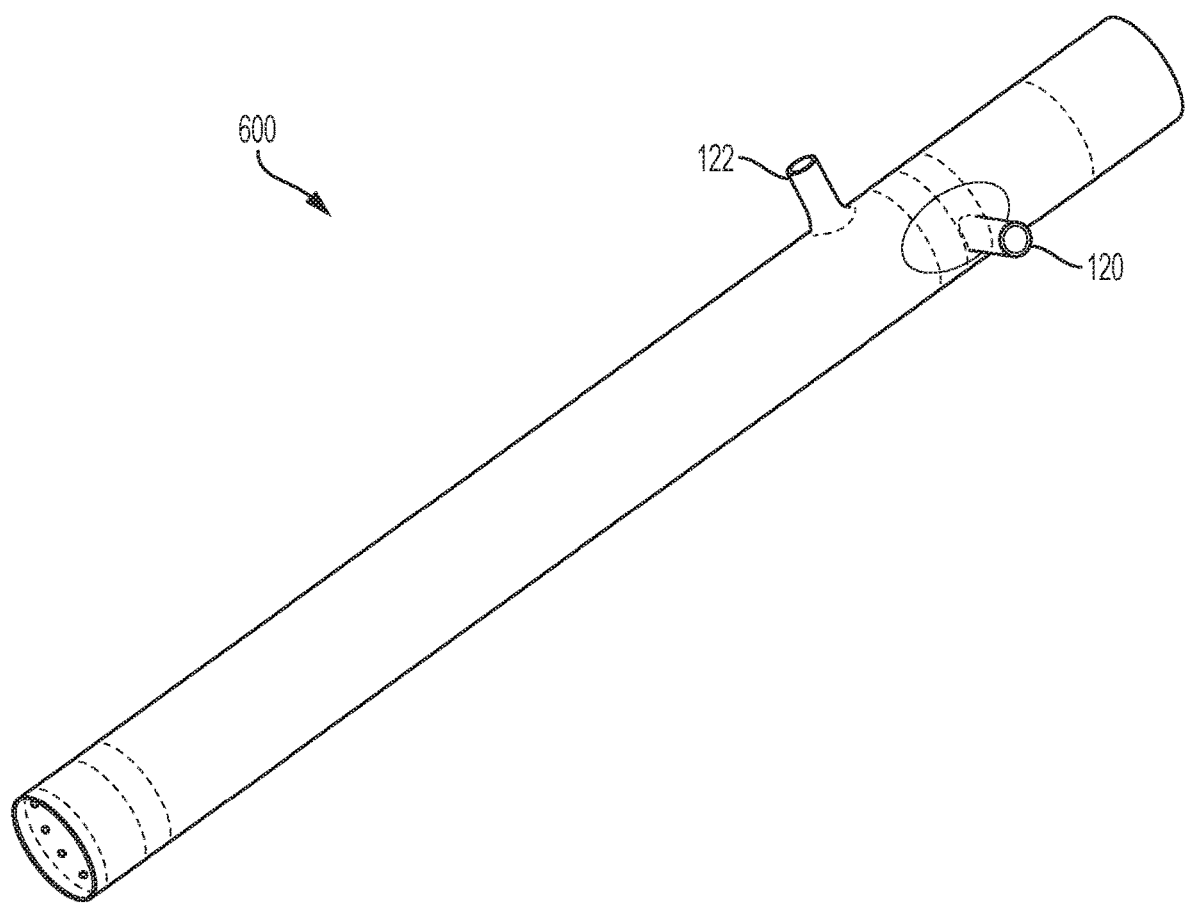
Figure 6B:
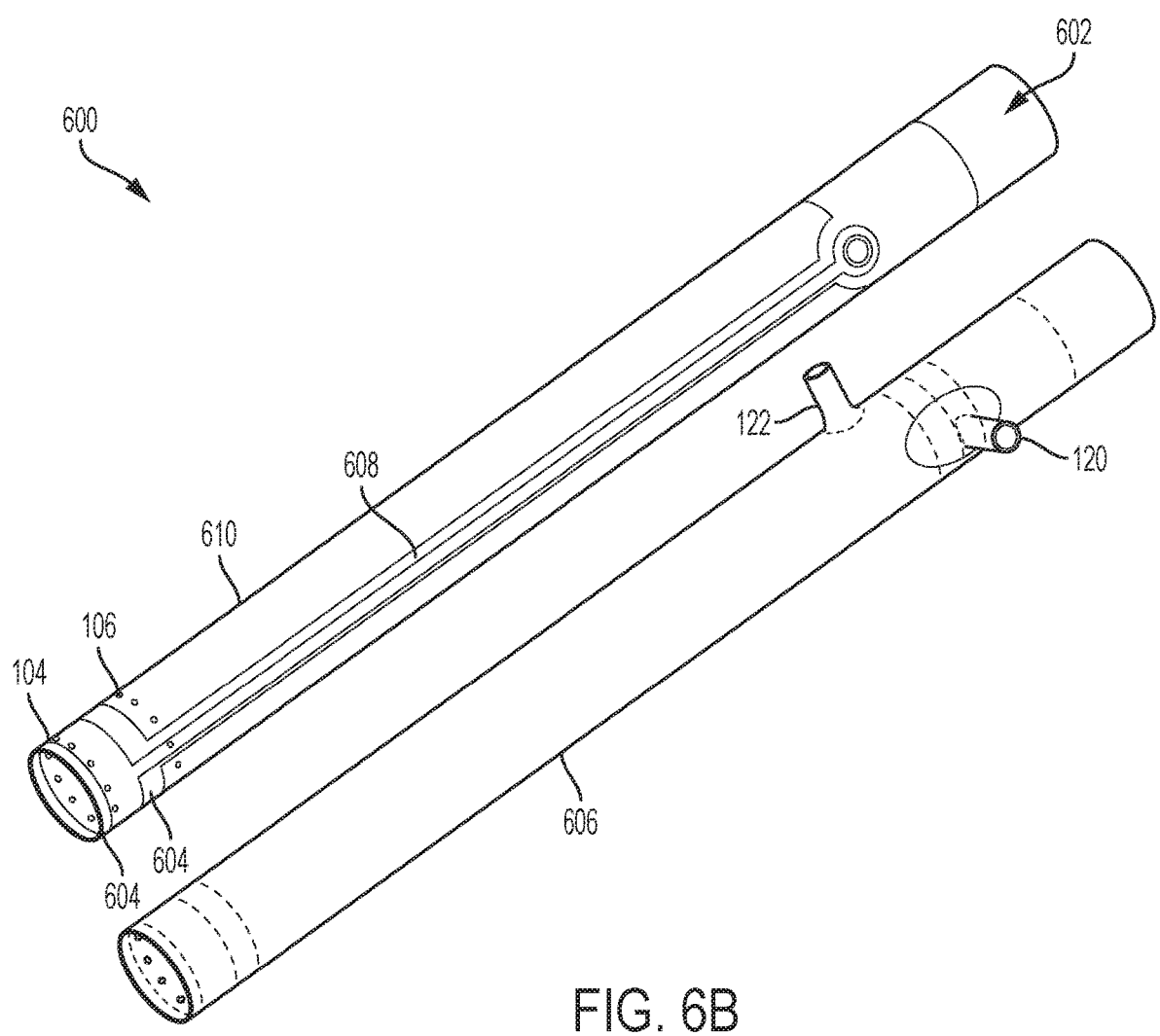
Figure 6C:
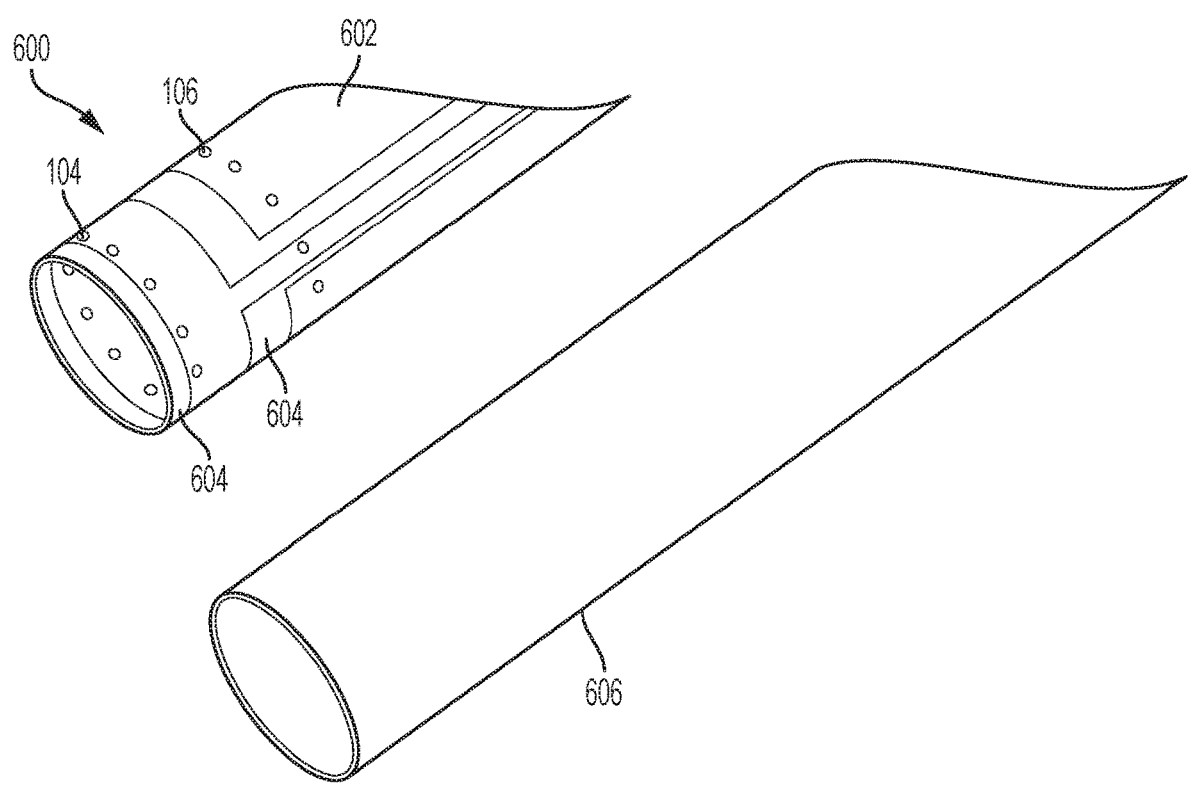
Figure 6D:
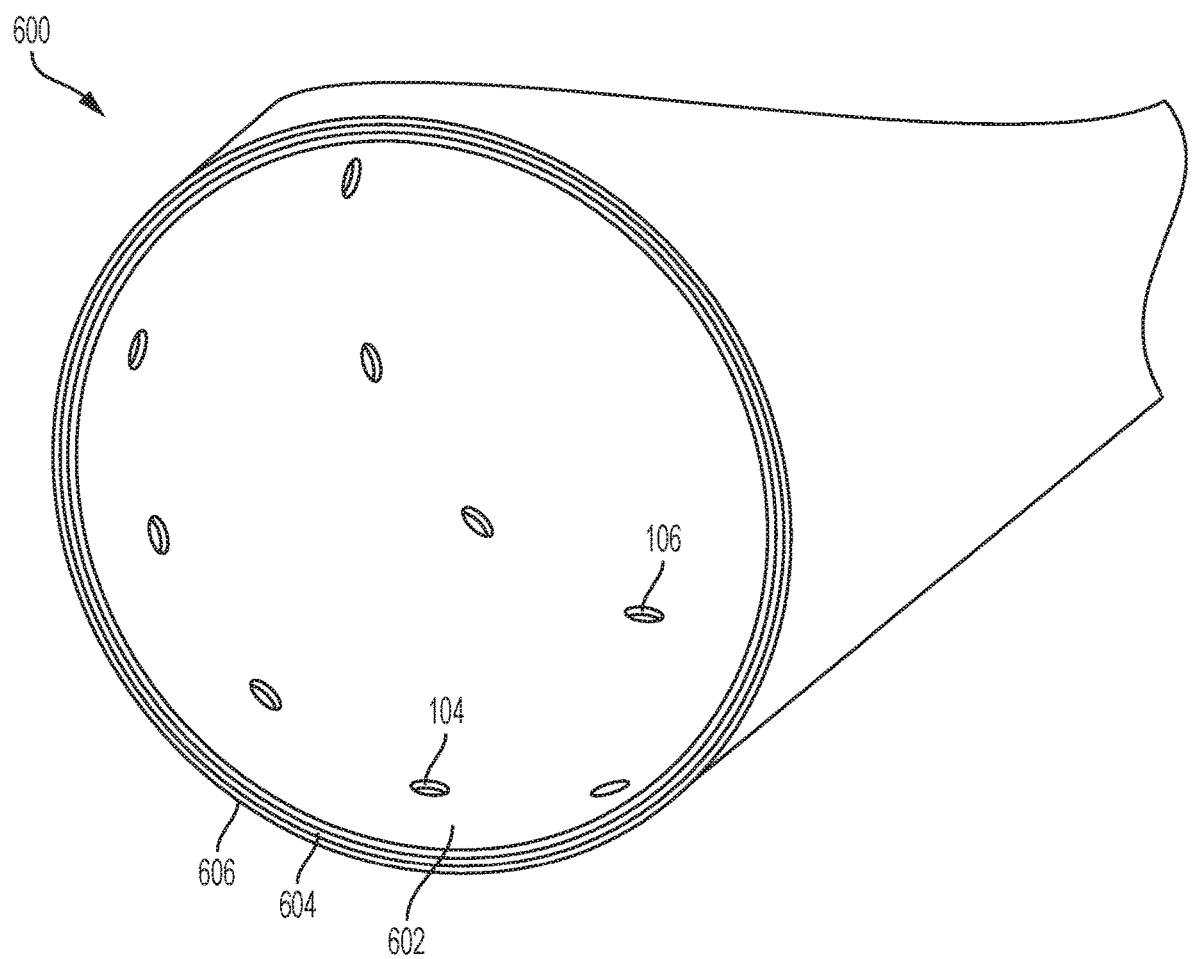
Figure 6E:
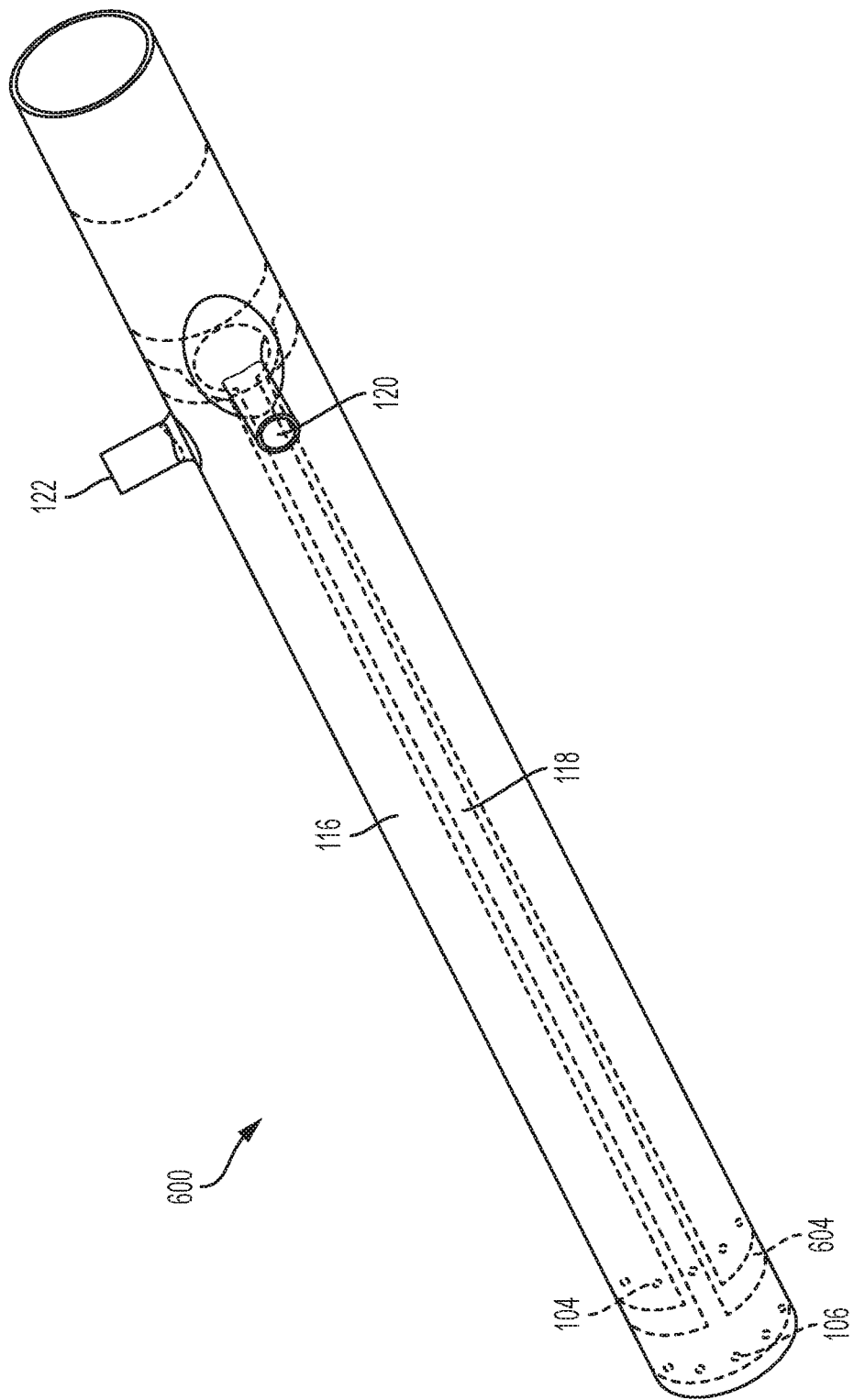
Figure 6F:
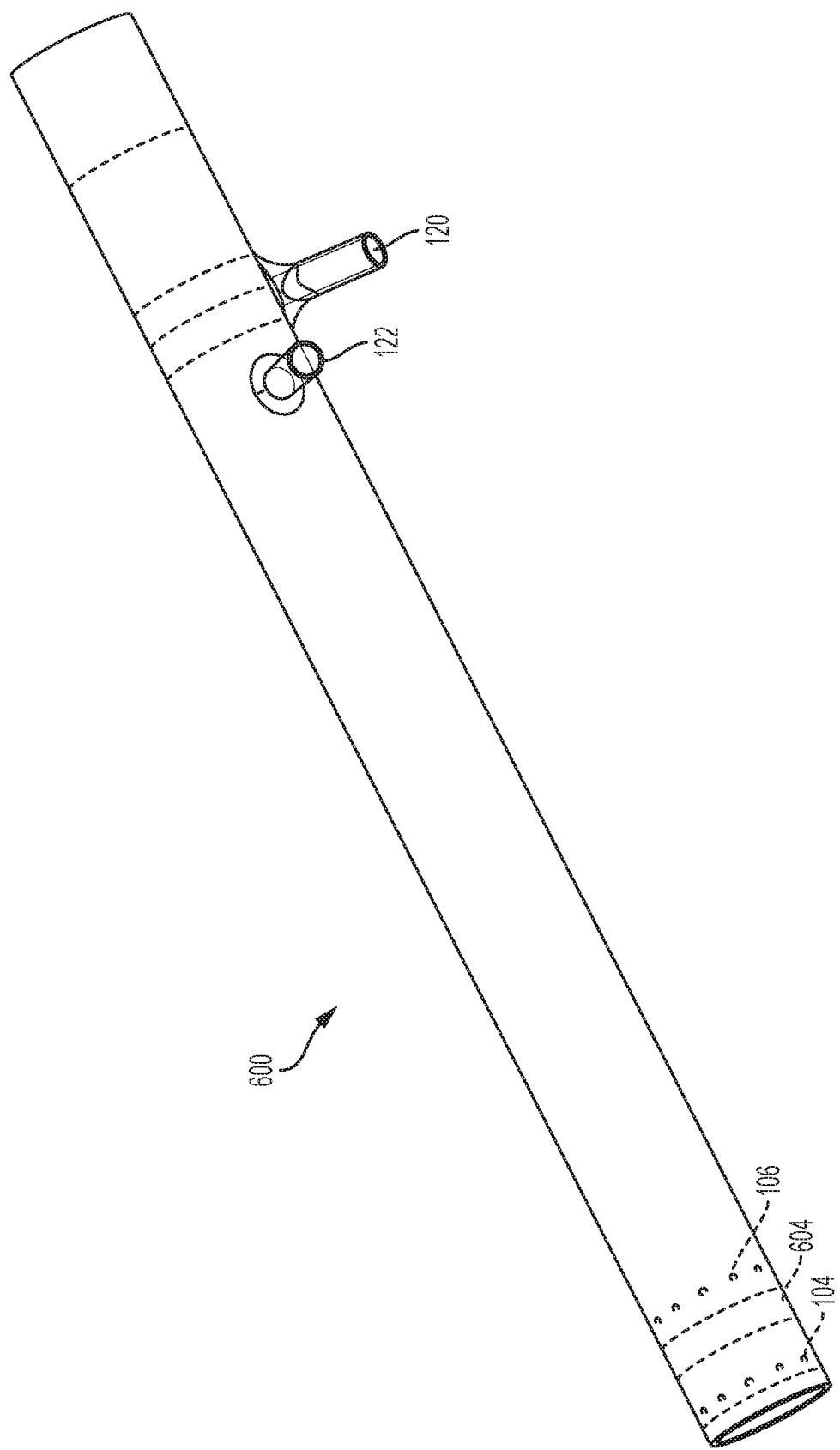
Figure 6H:
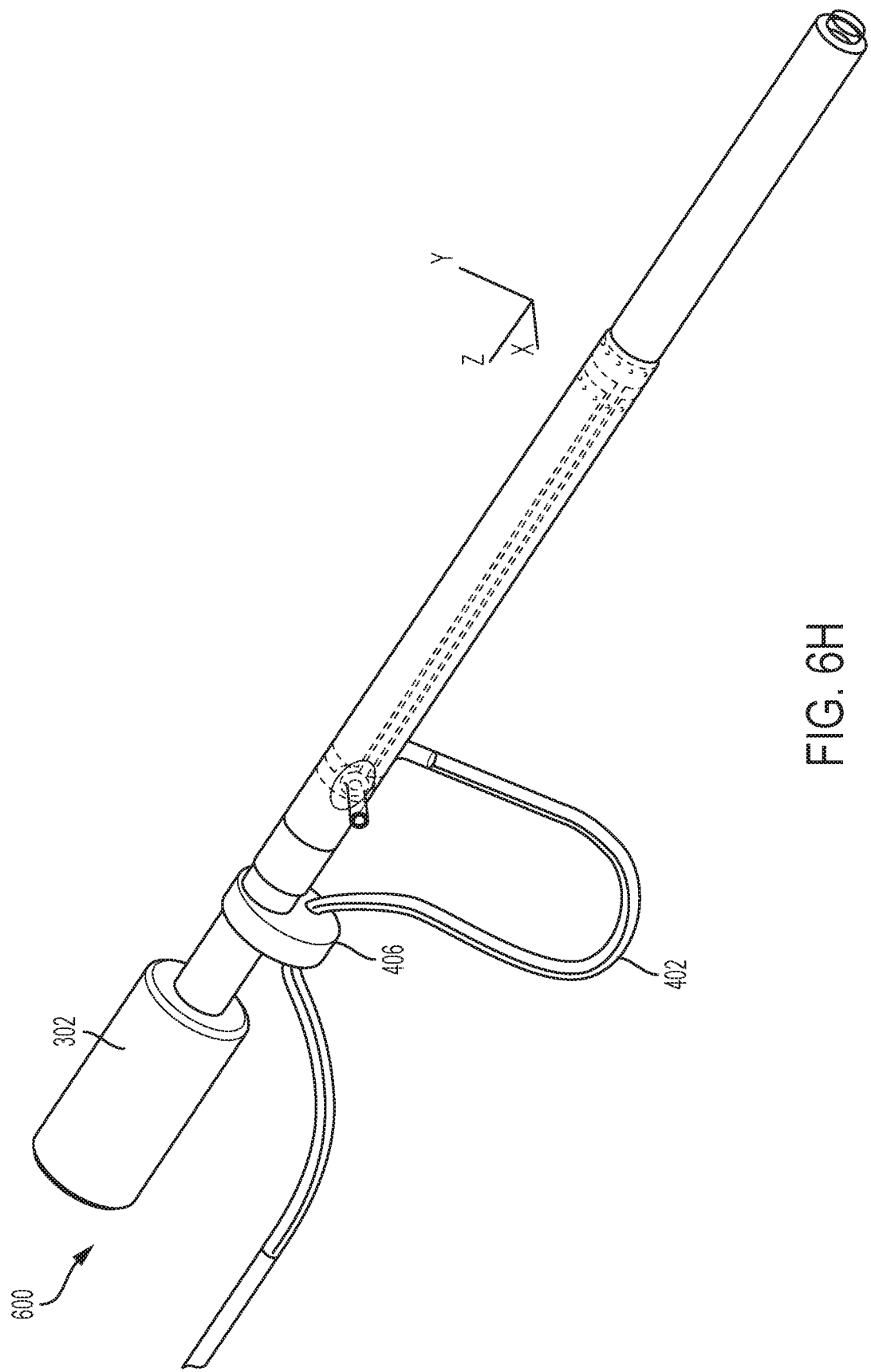

Referring now FIG. 4, the second mechanism of saline injection can be controlled by a button that is placed in line with saline tubing 402, between the pressurized saline bag and the saline input channel 118 on the trocar 100. This button 406 can be coupled to the hand held portion of the endoscopic camera 302 facilitating access of this button 406 to the camera operator. Once this button 406 is depressed, flow of saline through the tubing 402 and trocar 100 is initiated. Following either mechanism of saline injection, when the scope 302 is reinserted into the operative field, it is met with the stream of carbon dioxide at the most distal end of the trocar 100 which rids the lens 306 of any residual saline.

Figure 7C:
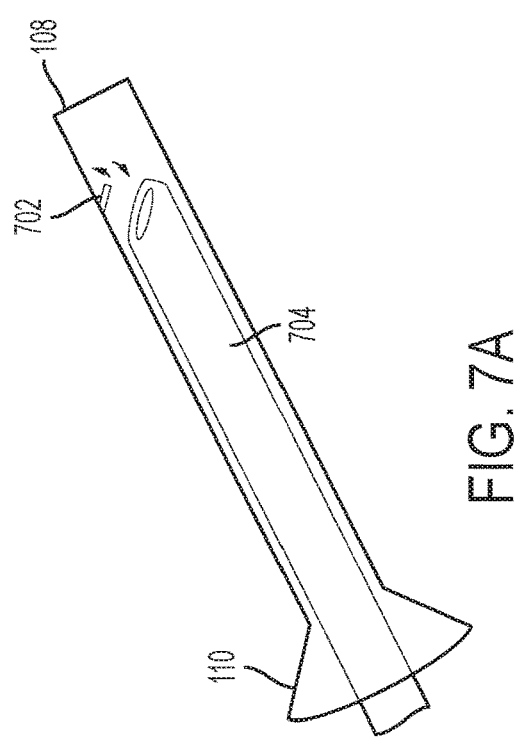
Figure 7D:
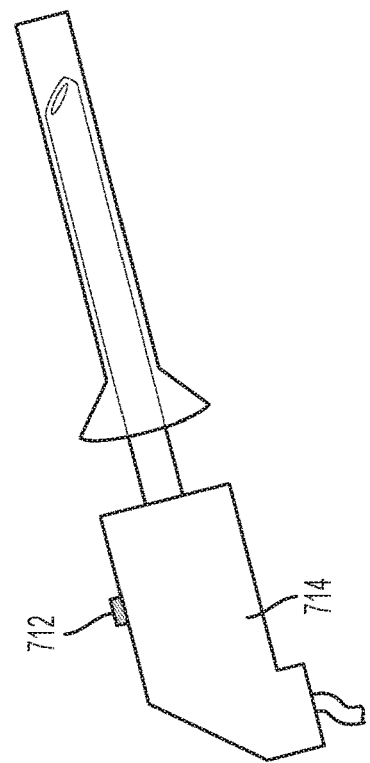

The embodiments of FIGS. 7C and 7D include a remote switch/sensor, where the switch/sensor 712, 716 is outside of the trocar. For example, in the embodiment of FIG. 7C, the switch/sensor 712 is located on handle 714 of the endoscope camera. In the embodiment of FIG. 7D, the switch/sensor 716 is adapted and configured for foot actuation.

Turning now to FIG. 7C, a manual switch/sensor 712 is located on handle 714 and communicatively coupled to the trocar to control fluid flow. In one embodiment, switch 712 can be adapted and configured to communicate directly or indirectly with the trocar to control the flow of liquid to the liquid outlet or outlets. Switch 712 can be a rocker switch, pressure switch, push button switch, or the like. In one embodiment, activation of switch 712 activates fluid flow and deactivation of switch 712 deactivates fluid flow. Switch 712 can be located at any position on handle 714 such that it can be activated and deactivated by a user. In one embodiment, switch 712 is activated when in a depressed state and deactivated when in a released state. However, in another embodiment, switch 712 may be activated when in a released state and deactivated when in a depressed state.

FIG. 7D illustrates an embodiment where the manual switch/sensor 716 is a foot-activated switch. Switch 716 can be communicatively coupled to the trocar and adapted and configured to communicate directly or indirectly with the trocar to control the flow of liquid out of the liquid outlet or outlets. In one embodiment, switch 716 includes a foot pedal that interacts with one of a rocker switch, pressure switch, push button switch, or the like. However, in other embodiments, switch 716 can include a switch and no foot pedal. Switch 716 can be positioned at ground level, proximate a user's foot for activation. In other embodiments, switch 716 can be position above ground level, in or on a housing, such that a user first lifts her foot before activating. In one embodiment, switch 716 is activated when in a depressed state and deactivated when in a released state. In another embodiment, switch 716 can be activated when in a released state and activated when in a depressed state.

Relay

In some embodiments, switches and/or sensors act as relays that are directly coupled to an electromechanically actuated valve such that activation of a switch or sensor based on the presence or absence of the endoscope at a particular location within the trocar directly actuates the valve to open or close.

In some embodiments, the valve lies within the same housing as button 406 and is configured such that the valve will open based on input from either the switch(es)/sensor(s) within the trocar or actuation of the button 406.

Valves, switches, and/or sensors (e.g., a switch/sensor on a trocar, endoscope handle, foot pedal, and the like) can be coupled using various mechanical linkages and/or wired or wireless interfaces.

Exemplary wired protocols include: Universal Serial Bus (USB), USB 2.0, IEEE 1394, Peripheral Component Interconnect (PCI), Ethernet, Gigabit Ethernet, and the like. The USB and USB 2.0 standards are described in publications such as Andrew S. Tanenbaum, *Structured Computer Organization Section* § 3.6.4 (5th ed. 2006); and Andrew S. Tanenbaum, *Modern Operating Systems* 32 (2d ed. 2001). The IEEE 1394 standard is described in Andrew S. Tanenbaum, *Modern Operating Systems* 32 (2d ed. 2001). The PCI standard is described in Andrew S. Tanenbaum, *Modern Operating Systems* 31 (2d ed. 2001); Andrew S. Tanenbaum, *Structured Computer Organization* 91, 183-89 (4th ed. 1999). The Ethernet and Gigabit Ethernet standards are discussed in Andrew S. Tanenbaum, *Computer Networks* 17, 65-68, 271-92 (4th ed. 2003).

Exemplary wireless protocols include: BLUETOOTH®, IEEE 802.11, IEEE 802.15.4, and the like. The BLUETOOTH® standard is discussed in Andrew S. Tanenbaum, *Computer Networks* 21, 310-17 (4th ed. 2003). The IEEE 802.11 standard is discussed in Andrew S. Tanenbaum, *Computer Networks* 292-302 (4th ed. 2003). The IEEE 802.15.4 standard is described in Yu-Kai Huang & Ai-Chan Pang, "A Comprehensive Study of Low-Power Operation in IEEE 802.15.4" in *MSWiM'07* 405-08 (2007).

Control Unit

In one embodiment, switches/sensor are communicatively coupled (e.g., through wired or wireless communication equipment and/or protocols) with a control unit. The control unit can be an electronic device programmed to control the operation of one or more switches regulating the flow of liquid (e.g., by regulating flow to liquid inlet 122). The control unit can be programmed to autonomously control fluid flow without the need for input from a medical professionals or can incorporate such inputs.

Control unit can be a computing device such as a microcontroller (e.g., available under the ARDUINO® or IOIO™ trademarks), general purpose computer (e.g., a personal computer or PC), workstation, mainframe computer system, and so forth. Control unit can include a processor device (e.g., a central processing unit or "CPU"), a memory device, a storage device, a user interface, a system bus, and a communication interface.

Processor can be any type of processing device for carrying out instructions, processing data, and so forth.

Memory device can be any type of memory device including any one or more of random access memory ("RAM"), read-only memory ("ROM"), Flash memory, Electrically Erasable Programmable Read Only Memory ("EEPROM"), and so forth.

Storage device can be any data storage device for reading/writing from/to any removable and/or integrated optical, magnetic, and/or optical-magneto storage medium, and the like (e.g., a hard disk, a compact disc-read-only memory "CD-ROM", CD-Re Writable "CDRW", Digital Versatile Disc-ROM "DVD-ROM", DVD-RW, and so forth). Storage device can also include a controller/interface for connecting to system bus. Thus, memory device and storage device are suitable for storing data as well as instructions for programmed processes for execution on processor.

User interface can include a touch screen, control panel, keyboard, keypad, display or any other type of interface, which can be connected to system bus through a corresponding input/output device interface/adapter.

Communication interface can be adapted and configured to communicate with any type of external device, including switches/sensors. Communication interface can further be adapted and configured to communicate with any system or network, such as one or more computing devices on a local area network ("LAN"), wide area network ("WAN"), the Internet, and so forth. Communication interface can be connected directly to system bus or can be connected through a suitable interface.

Control unit can, thus, provide for executing processes, by itself and/or in cooperation with one or more additional devices, that can include algorithms for controlling valves in accordance with the present invention. Control unit can be programmed or instructed to perform these processes according to any communication protocol and/or programming language on any platform. Thus, the processes can be embodied in data as well as instructions stored in memory device and/or storage device or received at user interface and/or communication interface for execution on processor.

Control unit can control the operation of the valves in a variety of ways. For example, the control unit can send electrical signals to the valves. Alternatively, the control unit can transmit instructions and/or parameters to the valves for implementation by the valves.

EQUIVALENTS

Although preferred embodiments of the invention have been described using specific terms, such description is for illustrative purposes only, and it is to be understood that changes and variations may be made without departing from the spirit or scope of the following claims.

INCORPORATION BY REFERENCE

The entire contents of all patents, published patent applications, and other references cited herein are hereby expressly incorporated herein in their entireties by reference.

The invention claimed is:

1. A trocar, comprising:
a central cylinder defining a central channel and having a distal end configured for insertion within a subject, the central channel configured to receive a distal end of an endoscope, the distal end of the central cylinder defining an opening to allow the distal end of the endoscope to extend out of the central channel to a distally advanced position;
one or more gas outlets located within the central cylinder proximate to the distal end of the central cylinder;
one or more liquid outlets located within the central cylinder proximate to the distal end of the central cylinder, wherein the one or more liquid outlets are configured to dispense a liquid when the distal end of the endoscope is withdrawn from the distally advanced position back into the central channel of the trocar to a position proximate to the one or more liquid outlets,
wherein the one or more gas outlets are configured to dispense gas to remove liquid from the distal end of the endoscope when the endoscope is distally advanced to a position adjacent to the one or more gas outlets;
a first coaxial cylinder surrounding at least a portion of the central cylinder, the first coaxial cylinder defining a substantially cylindrical channel extending to the one or more liquid outlets;
a second coaxial cylinder surrounding at least a portion of the first coaxial cylinder, the second coaxial cylinder defining a substantially cylindrical channel extending to the one or more gas outlets;
an optical sensor located proximate to the distal end of the central cylinder and proximate to the one or more liquid outlets, the optical sensor being configured to detect when the distal end of the endoscope has been withdrawn into the central channel and is proximate to the one or more liquid outlets; and a controller in communication with the optical sensor, the controller configured to control flow to the one or more liquid outlets so that a liquid is expelled from the one or more liquid outlets when the distal end of the endoscope is proximate to the liquid outlets.

2. The trocar of claim 1, wherein the one or more liquid outlets are positioned between about 1 cm and about 5 cm proximal of the one or more gas outlets.

3. The trocar of claim 1, wherein the one or more liquid outlets are positioned within about 6 cm of the distal end of the central cylinder.

4. The trocar of claim 1, further comprising:
a liquid inlet in fluid communication with the first coaxial cylinder.

5. The trocar of claim 1, further comprising:
a valve adapted and configured to control flow of the liquid to the one or more liquid outlets.

6. The trocar of claim 1, wherein the optical sensor is configured to communicate directly or indirectly to control flow of the liquid to the one or more liquid outlets.

7. The trocar of claim 1, further comprising:
an override switch.

8. The trocar of claim 7, wherein the override switch can be coupled to the endoscope.

9. The trocar of claim 7, wherein the controller is in communication with the override switch and further configured to control flow to the liquid outlets so that the liquid is expelled from the liquid outlets when the override switch is actuated.

10. The trocar of claim 1, further comprising:
a manual switch configured to communicate directly or indirectly to control flow of the liquid to the one or more liquid outlets.

11. The trocar of claim 10, wherein said manual switch is disposed on a handle of said endoscope.

12. The trocar of claim 10, wherein said manual switch comprises a foot pedal.

13. The trocar of claim 1, wherein at least the one or more liquid outlets are angled retrograde within the central cylinder such that the liquid expelled from the one or more liquid outlets is directed back toward the distal end of the endoscope.

14. A trocar, comprising:
a central cylinder defining a central channel and having a distal end configured for insertion within a subject, the central channel configured to receive a distal end of an endoscope, the distal end of the central cylinder defining an opening to allow the distal end of the endoscope to extend out of the central channel to a distally advanced position;

one or more gas outlets located within the central cylinder proximate to the distal end of the central cylinder;

one or more liquid outlets located within the central cylinder proximate to the distal end of the central cylinder, wherein the one or more liquid outlets are configured to dispense a liquid when the distal end of the endoscope is withdrawn from the distally advanced position back into the central channel of the trocar to a position proximate to the one or more liquid outlets;

a first coaxial cylinder surrounding at least a portion of the central cylinder, the first coaxial cylinder defining a substantially cylindrical channel extending to the one or more liquid outlets;

a second coaxial cylinder surrounding at least a portion of the first coaxial cylinder, the second coaxial cylinder defining a substantially cylindrical channel extending to the one or more gas outlets;

a gas inlet located at a proximal end of the outer cylinder; and a liquid inlet located at the proximal end of the outer cylinder.

15. The trocar of claim 14, wherein the substantially cylindrical channel extending to the one or more liquid outlets has a cross-sectional area at least 10 times a combined cross-section area of the one or more liquid outlets.

16. The trocar of claim 14, wherein the substantially cylindrical channel extending to the one or more gas outlets has a cross-sectional area at least 10 times a combined cross-section area of the one or more gas outlets.

17. The trocar of claim 14, further comprising one or more sensors located proximate to the distal end of the central cylinder and proximate to the one or more liquid outlets, the one or more sensors being configured to detect when the distal end of the endoscope has been withdrawn into the central channel and is proximate to the one or more liquid outlets, the one or more sensors configured to communicate directly or indirectly with a valve to control flow of the liquid to the one or more liquid outlets.

18. The trocar of claim 14, wherein the one or more liquid outlets are positioned within about 6 cm of the distal end of the central cylinder.

* * * * *